United States Patent
Gooding et al.

(10) Patent No.: US 10,929,976 B2
(45) Date of Patent: Feb. 23, 2021

(54) METHOD AND APPARATUS FOR ASSESSING IMAGE REGISTRATION

(71) Applicant: Mirada Medical Limited, Oxford (GB)

(72) Inventors: Mark Gooding, Oxford (GB); Timor Kadir, Oxford (GB)

(73) Assignee: Mirada Medical Limited, LLC, Oxford (GB)

(*) Notice: Subject to any disclaimer, the term of this patent is extended or adjusted under 35 U.S.C. 154(b) by 51 days.

(21) Appl. No.: 15/556,904

(22) PCT Filed: Feb. 23, 2016

(86) PCT No.: PCT/EP2016/053714
§ 371 (c)(1),
(2) Date: Sep. 8, 2017

(87) PCT Pub. No.: WO2016/142166
PCT Pub. Date: Sep. 15, 2016

(65) Prior Publication Data
US 2018/0247412 A1    Aug. 30, 2018

(30) Foreign Application Priority Data
Mar. 12, 2015   (GB) .................................... 1504188

(51) Int. Cl.
*A61B 90/00* (2016.01)
*G06T 11/00* (2006.01)
(Continued)

(52) U.S. Cl.
CPC ............ *G06T 7/0016* (2013.01); *A61B 90/36* (2016.02); *G06T 7/30* (2017.01); *G06T 7/38* (2017.01);
(Continued)

(58) Field of Classification Search
None
See application file for complete search history.

(56) References Cited

U.S. PATENT DOCUMENTS 7,933,380 B2 *  4/2011  Nord .................... A61N 5/1049
                                                         378/65
10,083,510 B2 *  9/2018  Franz ........................ G06T 7/32
(Continued)

FOREIGN PATENT DOCUMENTS

DE    102011080905 A1 *  2/2013   ............. G16H 40/63
DE    102011080905 A1     2/2013

OTHER PUBLICATIONS

K Murphy et al., "Evaluation of Registration Methods on Thoracic CT: The EMPIRE10 Challenge," IEEE Transactions on Medical Imaging, vol. 30, Issue: 11, pp. 1901-1920, May 31, 2011 (Year: 2011).*
(Continued)

*Primary Examiner* — Soo Shin
(74) *Attorney, Agent, or Firm* — Optimus Patents US, LLC

(57) ABSTRACT

A method and apparatus for assessing image registration. The method comprises obtaining image datasets for the first and second medical images and registration data representing the registration from the first medical image to the second medical image, collating use-case information for the image registration, deriving a set of at least one measurement and assessment criteria therefor based at least partly on the collated use-case information, performing the at least one measurement on at least one of the obtained image datasets and the obtained registration data to derive at least one measurement value, applying the assessment criteria for the at least one measurement to the at least one measurement value to derive at least one assessment result, (Continued)

and outputting an indication of the at least one assessment result.

17 Claims, 9 Drawing Sheets

(51) Int. Cl.
    *G06T 7/00*         (2017.01)
    *G06T 7/30*         (2017.01)
    *G06T 7/38*         (2017.01)
    *G16H 10/60*      (2018.01)
    *G16H 30/20*      (2018.01)
    *G16H 30/40*      (2018.01)

(52) U.S. Cl.
    CPC .......... *G06T 11/001* (2013.01); *G06T 11/008* (2013.01); *G16H 10/60* (2018.01); *G16H 30/20* (2018.01); *A61B 2090/364* (2016.02); *A61B 2090/3762* (2016.02); *G06T 2207/30004* (2013.01); *G06T 2207/30012* (2013.01); *G06T 2211/40* (2013.01)

(56) References Cited

U.S. PATENT DOCUMENTS

| | | | | |
|---|---|---|---|---|
| 10,235,759 | B2* | 3/2019 | Kosmecki | G06T 7/149 |
| 10,255,679 | B2* | 4/2019 | Yin | G06T 19/20 |
| 2005/0111718 | A1* | 5/2005 | MacMahon | G06T 7/0012 |
| | | | | 382/130 |
| 2012/0051607 | A1* | 3/2012 | Nord | G06F 19/321 |
| | | | | 382/128 |
| 2013/0004044 | A1* | 1/2013 | Ross | G06T 7/136 |
| | | | | 382/131 |
| 2013/0251218 | A1* | 9/2013 | Eriksson Jarliden | G06T 7/30 |
| | | | | 382/128 |
| 2014/0254904 | A1* | 9/2014 | Matthews | G06T 7/30 |
| | | | | 382/131 |
| 2015/0331995 | A1* | 11/2015 | Zhao | G16H 40/63 |
| | | | | 705/2 |
| 2016/0067007 | A1* | 3/2016 | Piron | G16H 50/70 |
| | | | | 705/3 |
| 2017/0243336 | A1* | 8/2017 | Zou | G06T 5/50 |

OTHER PUBLICATIONS

Evaluating Image Registration Using NIREP Joo Hyun Song, Gary E. Christensen, Jeffrey A. Hawley, Ying Wei, and Jon G. Kuhl.

A flexible registration and Evaluation engine (f.r.e.e.) Ralf Floca, Hartmut Dickhaus Department of Medical Informatics, Institute for Medical Biometry and Informatics, University of Heidelberg, rm Neuenheimer Feld 400, D-69120 Heidelberg, Germany.

IEEE Transactions on Medical Imaging, vol. 30, Issue 11, Published 2011, Keelin Murphy et al, "Evaluation of Registration Methods on Thoracic CT: The EMPIRE 10 Challenge", pp. 1901-1920 (Murphy et al) See whole document particularly section IV titled "Evaluation" Relevant to claims 1-5 and 8-13.

Computer Methods and Programs in Biomedicine, vol. 87, No. 2, Published 2007, Ralf Floca et al, "A flexible registration and evaluation engine (f.r.e.e.)", pp. 81-92 (Floca et al) See whole document particularly section 3.4 titled "Optimisation of parameterisation" and figure 10 Relevant to claims 1-13.

GB Patent Office, Patents Act 1977: Examination Report under Section 18(3), Application No. GB1504188.2, dated Jul. 4, 2019.

Astrid Franz, Nicole Schadewaldt, Heinrich Schulz, Torbjørn Vik, Lisa Kausch, Jan Modersitzki, Rafael Wiemker, Daniel Bystrov, "Annotation-free probabilistic atlas learning for robust anatomy detection in CT images," Proc. SPIE 9413, Medical Imaging 20 38 (Mar. 20, 2015); doi: 10.1117/12.2082030.

Astrid Franz, Nicole Schadewaldt, Heinrich Schulz, Torbjørn Vik, Martin Bergtholdt, Daniel Bystrov, "Precise anatomy localization in CT data by an improved probabilistic tissue type atlas," Proc. SPIE 9784, Medical Imaging 2016: Image Processing, 978444 (Mar. 21, 2016), doi: 10.1117/12.2209036.

Brock et al.; Use of Image registration and Fusion Algorithms and Techniques in Radiotherapy: Report of the AAPM Radiation Therapy Committee Task Group No. 132; American Association of Physicists in Medicine; Med..Phys. 44(7) Jul. 2017; pp. e43-e76.

* cited by examiner

METHOD AND APPARATUS FOR ASSESSING IMAGE REGISTRATION

FIELD OF THE INVENTION

This invention relates to a method and apparatus for assessing image registration, and in particular to assessing registration between a first medical image and a second medical image.

BACKGROUND OF THE INVENTION

In the field of medical imaging, a variety of technologies can be used to investigate biological processes and anatomy. The following examples are types of scan that may be used to provide medical images: X-Ray; Computed Tomography (CT); Ultrasound (US); Magnetic Resonance Imaging (MRI); Single Photon Emission Tomography (SPECT); and Positron Emission Tomography (PET). Each type of scan is referred to as an 'imaging modality'.

Typically, a scan provides a 'dataset'. The dataset comprises digital information about the value of a variable at each of many spatial locations in either a two-dimensional or (more typically) a three-dimensional space. The variable may typically be an intensity measurement. The intensity may be, for example, an indication of the X-Ray attenuation of the tissue at each particular point.

In the case of a three-dimensional dataset, the element of the scan image located at a particular spatial location is typically referred to as a 'voxel'. A voxel is therefore analogous to a 'pixel' of a conventional 2-Dimensional image.

It is to be understood that the term 'image' used herein may refer to either a three-dimensional volumetric image or a two-dimensional planar image, unless otherwise stated or as may be apparent from the context within which the term is used.

Image registration is the process by which an alignment, or spatial correspondence, between two or more images is determined. Registration of medical images is useful for many clinical applications. Examples include:
improving workflow for treatment monitoring by using the correspondence found through image registration to link cross-hairs in follow-up imaging such that the same anatomical location can be studied more easily;
using registration to transfer contours between image modalities to enable multiple different image modalities to be used for contouring when performing radiotherapy treatment planning;
etc.

A wide range of image registration algorithms have been proposed that differ in their application focus. For example image registration may use rigid, affine or deformable transformation models and may be performed between images of the same modality, or images of different imaging modalities. The alignment may also be between images for the same subject (e.g. for follow-up imaging) or between different subject (e.g. atlas-based auto-contouring).

Prior art references [1] and [2] below (listed at the end of the Background of the invention) are registration algorithm review publications that provide a more thorough overview of the current principal registration algorithms.

Despite the progress that has been made in image registration performance, the quality of the results in practice varies and is not guaranteed. Therefore, the quality of the alignment produced by a particular registration algorithm between images for a patient should be assessed prior to being relied upon in clinical use. Current clinical practice is to perform this assessment visually. Typically both anatomical alignment and deformation field plausibility are assessed in a qualitative manner. Prior art reference [3] describes such a typical qualitative visual assessment.

However, such visual assessment is both subjective (i.e. subject to inter- and intra-user variability) and time consuming and laborious (requiring the user to check the entire volume). Moreover, certain desirable properties of the alignment, such as inverse consistency (the property that the registration would have been the same if the images had been reversed) cannot be assessed visually.

An objective and quantitative measure of assessing registration quality is required.

A number of quantitative measures of registration accuracy have been proposed. For example, prior to deploying a particular algorithm into a clinical application, it is first necessary to test and validate the algorithm on a representative set of patients. Typically, experiments will be performed to determine the accuracy of the registration using one or more of the following measures:
Measuring Target Registration Error (TRE) by using manually placed paired-landmarks on pairs of real patient images, and measuring the alignment error before and after image registration, such as described in prior art reference [4];
Measuring registration error using known deformations from synthetically deformed images, such as described in prior art reference [5];
Measuring registration error from surrogate measurements on hardware phantoms, such as described in prior art reference [6]; and
Measuring the overlap of regions of interest (or segmentations) on marked up images before and after registration, such as described in prior art reference [7].

Such quantitative validation methods, while effective in an empirical study setting, are impractical for use in clinical practice because they require establishing a 'ground-truth' correspondence between the images in the test set with which to assess the accuracy of the registration. This involves the manual identification of a large set of corresponding locations or delineations on the images.

It is possible to evaluate the plausibility of a registration in the absence of ground-truth alignment information. Known techniques for such evaluations include:
Testing the inverse consistency by performing registration in both directions, such as described in prior art reference [8];
Testing the consistency of transformations around 3 images, known as transitivity, such as described in prior art reference [9]; and
Measuring parameters of the deformation field, such as the Determinant of the Jacobian, such as described in prior art reference [10].

Notably, none of the above methods directly measure the accuracy of the alignment. Instead, they attempt to measure properties of the deformation field that are desirable in a mathematical sense. However, scoring well against any one of the above criteria does not necessarily imply a good alignment. Consequently such methods cannot be used on their own to assess registration quality.

A number of methods have been proposed that utilize multiple measures:
In prior art reference [11], a set of measurements were used to assess registration quality including Lung boundary alignment, Fissure alignment, Manual landmark error, Determinant of the Jacobian. The study sought to compare different registration algorithms, therefore the feature measures were converted to the performance ranks and the rank in each category was averaged to give a score for the registration method. While this approach generated a single measure from multiple measures, it relied on manual mark-up of ground-truth and produced a ranking of registration methods, rather than a means to assess whether a particular result had sufficient quality. Hence this approach could not be used to assess the quality of a registration result for a particular patient.

In prior art reference [12] four measures were used to evaluate registration quality: TRE, Divergence of the deformation, Shear of the Deformation, Transitivity. Pass/fail thresholds were applied to each of these measures, and a percentage of voxels exceeding the limits were reported for each measure. This framework relies on manual mark-up for TRE and transitivity, and a third image for the transitivity test. Moreover, the thresholds are not organ or application specific but are fixed for all use-cases and body parts. In practice, a good registration in one part of the body and utilized for one clinical use-case might exhibit quite different properties than those of another. Thus this system is not practical for clinical use.

In prior art reference [13] a set of 30 image and deformation field features were calculated for each registration. A machine learning approach was adopted to "learn" to classify good and bad registrations using cases with ground-truth landmark correspondences. The advantage of the system is that, once trained, it does not require any ground-truth annotation. However, the disadvantage is that it does not provide the user with any explanation or insight into the final classification; it outputs a single classification either good or bad. Therefore, a clinical user will not be able to assess the reliability of the system on a particular patient nor understand why it has produced a certain result. In practice, the user would need to interpret the quality assessment in light of the clinical situation. For example, volume change in a tumour might be acceptable when registering images of an oncology patient before and after therapy. In contrast, it would not be acceptable when using a PET/CT or MRI registered to a planning CT to guide the target definition because the different imaging modalities should be imaging the same anatomy at (nearly) the same time. Finally, it would not be practical to train such a system to provide this level of detail for all tumour sites, use-case and modalities.

In [14], multiple quality maps are generated from simple features in a non-medical application. The analysis of these features are combined but for the purpose of detecting systematic errors such as those from the camera system. The examples are from optical imaging, and include detecting Lens Distortion errors. In this approach features are combined to detect individual error types, but not to provide a single quality score. The importance of the sources of error is not considered and as with the system proposed in [13], the proposed method cannot provide any insight to the result.

Thus, there remains a need for a system that can quantitatively assess registration quality in an application and disease specific manner that is practical to be used for every patient in clinical setting and provides simple yet meaningful reporting of quality to the end-user.

PRIOR ART REFERENCES

[1] J B Maintz and M A Viergever. A survey of medical image registration. Medical Image Analysis 1998; 2(1): 1-36
[2] D L G Hill et al. Medical Image registration. Physics in medicine and biology. 2001; 46(3):R1
[3] J M Fitzpatrick et al. Visual assessment of the accuracy of retrospective registration of M R and C T images of the brain. IEEE Trans Med Imag 1998; 17(4):571-585
[4] R Castillo et al. A framework for evaluation of deformable image registration spatial accuracy using large landmark point sets. Physics in medicine and biology. 2009; 54(7):1849-1870
[5] H Wang et al. Validation of an accelerated 'demons' algorithm for deformable image registration in radiation therapy. Physics in medicine and biology. 2005; 50:2887-2905
[6] R Kashani et al. Objective assessment of deformable image registration in radiotherapy: A multi-institution study. Medical Physics 2008; 35(12)5944-5953
[7] N E Makris et al. Validation of simplified dosimetry approaches in 89 Zr-PET/CT: The use of manual versus semi-automatic delineation methods to estimate organ absorbed doses. Medical Physics 2014; 41:102503
[8] T B Nyeng et al. Clinical validation of a 4D-CT based method for lung ventilation measurement in phantoms and patients. Acta Oncologica. 2011; 50(6):897-907
[9] G E Christensen et al. Introduction to the non-rigid image registration evaluation project (NIREP). Biomedical image registration. Springer Berlin Heidelberg, 2006. 128-135
[10] R Varadhan et al. A framework for deformable image registration validation in radiotherapy clinical applications. J Appl Clin Med Phys. 2013; 14(1):4066-4100
[11] K Murphy et al. Evaluation of Registration Methods on Thoracic CT: The EMPIRE10 Challenge. IEEE Trans Med Imag 2011; 30(11):1901-1920
[12] P W H Wittendorp et al. Validation of three deformable image registration algorithms using the TEST method. 2nd ESTRO Forum. 2013. OC-0061
[13] S E A Muenzing et al. Automatic detection of registration errors for quality assessment in medical image registration. SPIE Medical Imaging 2009; 72590K-72590K
[14] B Moller and S Posch. An integrated analysis concept for errors in image registration. Pattern Recognition and Image Analysis 2008; 18(2):201-206.

SUMMARY OF THE INVENTION

Accordingly, the invention seeks to mitigate, alleviate or eliminate one or more of the abovementioned disadvantages singly or in any combination.

According to a first aspect of the present invention, there is provided a method of assessing image registration between a first medical image and a second medical image. The method comprises obtaining image datasets for the first and second medical images and registration data representing the registration from the first medical image to the second medical image, collating use-case information for the image registration, deriving a set of at least one measurement and assessment criteria therefor based at least partly on the collated use-case information, performing the at least one measurement on at least one of the obtained image datasets and the obtained registration data to derive at least one measurement value, applying the assessment criteria for the at least one measurement to the at least one measurement value to derive at least one assessment result, and outputting an indication of the at least one assessment result.

In this manner, the method utilises a set of measurements and assessment criteria therefor relevant to the particular use-case to assess the accuracy of the registration between two medical images. This enables image registration accuracy to be assessed in a quantitative manner across a range of clinical applications in a focussed manner.

In some optional embodiments, the registration data may comprise parameters for a transformation model of a registration algorithm used to perform the registration from the first medical image to the second medical image.

In some optional embodiments, the use-case information may comprise at least one of:
  information input by a user;
  information loaded from local memory; and
  information loaded from at least one external data storage device.

In some optional embodiments, the use-case information may comprise at least one of:
  information relating to a clinical task being performed;
  a clinical question being asked;
  information relating to a disease;
  information relating to a patient; and
  information relating to at least one region of interest.

In some optional embodiments, the set of at least one measurement may comprise at least one of:
  at least one measure of the biological plausibility of a deformation field of the registration from the first medical image to the second medical image;
  at least one surrogate measure of anatomical matching accuracy; and
  at least one numerical property of the registration.

In some optional embodiments, the set of at least one measurement may be derived by selecting a predefined set of at least one measurement from a plurality of predefined sets of at least one measurement.

In some optional embodiments, the set of at least one measurement may be derived by identifying a predefined use-case scenario that most closely matches the collated use-case information, and selecting a set of at least one measurement with which the identified use-case scenario is associated.

In some optional embodiments, the set of at least one measurement may be derived by selecting a set of measurements predefined as being relevant to use-case parameters within the collated use-case information.

In some optional embodiments, the indication of the at least one assessment result may comprise a registration assessment score generated from the at least one assessment result.

In some optional embodiments, the indication of the at least one assessment result may comprise a registration assessment record.

In some optional embodiments, the indication of the at least one assessment result may be output by being displayed on a screen to a user.

In some optional embodiments, the indication of the at least one assessment result may comprise at least one of:
  displaying the at least one assessment result graphically to a user in the form of a colour coding overlaid over at least one of the medical images, and
  displaying the at least one assessment result graphically to a user with quantitative information highlighted over at least one of the medical images.

In some optional embodiments, the indication of the at least one assessment result may be output by being stored within a data storage device.

In some optional embodiments, the method may further comprise receiving at least one indication from a user about the registration assessment result for at least one region, updating quality assessment data used to derive quality assessment protocols based at least partly on the received at least one indication from a user about the registration assessment result for at least one region.

According to a second aspect of the present invention, there is provided a medical imaging system comprising at least one image registration assessment component. The at least one image registration assessment component is arranged to obtain image datasets for the first and second medical images and registration data representing the registration from the first medical image to the second medical image, collate use-case information for the image registration, derive a set of at least one measurement and assessment criteria therefor based at least partly on the collated use-case information, perform the at least one measurement on at least one of the obtained image datasets and the obtained registration data to derive at least one measurement value, apply the assessment criteria for the at least one measurement to the at least one measurement value to derive at least one assessment result, and output an indication of the at least one assessment result.

According to a third aspect of the present invention there is provided a non-transitory computer program product having executable program code stored therein for assessing image registration. The program code is operable for obtaining image datasets for the first and second medical images and registration data representing the registration from the first medical image to the second medical image, collating use-case information for the image registration, deriving a set of at least one measurement and assessment criteria therefor based at least partly on the collated use-case information, performing the at least one measurement on at least one of the obtained image datasets and the obtained registration data to derive at least one measurement value, applying the assessment criteria for the at least one measurement to the at least one measurement value to derive at least one assessment result, and outputting an indication of the at least one assessment result.

The non-transitory computer program product may comprise at least one from a group including: a hard disk, a CD-ROM, an optical storage device, a magnetic storage device, a Read Only Memory, ROM, a Programmable Read Only Memory, PROM, an Erasable Programmable Read Only Memory, EPROM, an Electrically Erasable Programmable Read Only Memory, EEPROM, and a Flash memory.

These and other aspects of the invention will be apparent from and elucidated with reference to the embodiments described hereinafter.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION OF THE PREFERRED EMBODIMENTS

The present invention provides a method and apparatus for quantitatively assessing image registration in an application and disease specific manner that is capable of practical use in relation to individual patients in clinical settings, and that provides simple yet meaningful reporting of quality to the user.

The inventors have recognised that while it may not be possible to definitively determine that a particular registration result is good in the absence of ground-truth correspondences, it is possible to use multiple measures to determine whether there are definitely problems in the registration.

For example, consider the situation where a user would like to register a PET/CT to a radiation therapy planning CT. In this situation, we can expect that the images were acquired at nearly the same date and hence the normal and disease anatomy should match well. We can expect that bones should move rigidly in an articulated fashion but do not change in volume and that soft tissue should not compress or expand in volume. Areas filled with air, such as the lungs, can change volume. The solution proposed by the inventors (i) measures these aspects of the images and the deformation, (ii) tests them against a pre-determined set of criteria that is optimised for the particular use-case, and in some examples (iii) produces a report that summarises which measurements passed and which failed. The combined score is then the fraction of those that passed out of all tests.

In a different example the user may like to register two planning CTs from two different treatment courses of radiation therapy for a given patient. Such a situation typically arises if patients have recurring disease and the clinical team must decide if re-treatment is possible without overdosing the non-diseased organs. In this situation, we can expect that the images were acquired months or even years apart and that the patient's diseased regions have changed significantly. Tumours may have shrunk and re-grown in the same or adjacent areas. However, assuming the tumour is in soft tissue, the bones should not change in volume and should move rigidly. However, we might expect some weight change and gain or loss in tissue mass. This might be in the fat or the organ tissue but we might expect volume to be approximately conserved but not to such a precise tolerance as in the first example. Weighing the patient could also be in input factor into the criteria. In this situation, our invention would use a different set of measurements and criteria that is specifically setup for this situation. For example, the system could use a wider range of thresholds to assess the change in volume in soft tissue areas than in the first example.

It is clear from the above examples that it is necessary to adapt the system according to clinical question or use-case, disease site and state and modality and that a single set of measurements and criteria is insufficient for all clinical use-cases.

Figure 1:
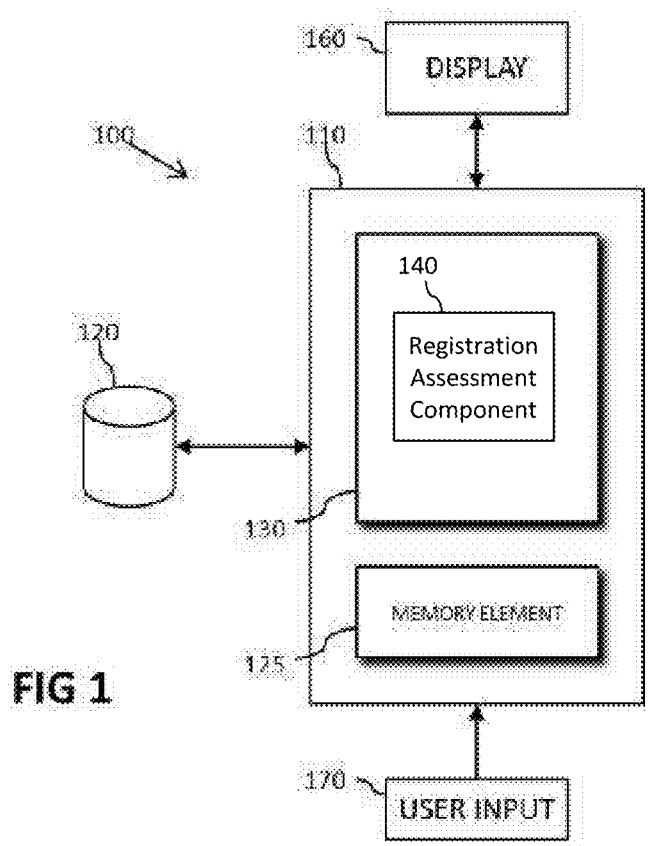
FIG. 1 illustrates a simplified block diagram of an example of a medical imaging system.

Referring now to FIG. 1, there is illustrated a simplified block diagram of an example of a medical imaging system 100 arranged to enable medical images to be displayed to a user. Such a medical imaging system 100 may comprise, say, a picture archiving and communication system (PACS), an advanced visualisation workstation, an imaging acquisition workstation, a web based or cloud based medical information and image system, a Radiotherapy treatment Planning System (TPS), or the like.

In the illustrated example, the medical imaging system 100 comprises one or more user terminals 110, for example comprising a workstation or the like, arranged to access medical images stored within, for example, a database 120 or other data storage apparatus. In the illustrated example, a single database 120 is illustrated. However, it will be appreciated that the user terminal 110 may be arranged to access medical images from more than one data storage apparatus. Furthermore, in the illustrated example the database 120 is illustrated as being external to the user terminal 110. However, it will be appreciated that the user terminal 110 may equally be arranged to access medical images stored locally within one or more internal memory elements, such as the memory element illustrated generally at 125. The user terminal 110 further comprises one or more signal processing modules, such as the signal processing module illustrated generally at 130. The signal processing module(s) is/are arranged to executing computer program code, for example stored within the memory element 125. In the illustrated example, the signal processing module(s) 125 is/are arranged to execute computer program code comprising one or more image registration assessment component(s) 140, the image registration assessment component(s) 140 being arranged to perform measurements for registrations between medical images, apply assessment criteria to the measurements, and output registration assessment results. The medical imaging system 100 may further comprise one or more user input devices, such as illustrated generally at 170, to enable a user to interact with computer program code etc. executing on the signal processing module(s) 125.

Figure 2:
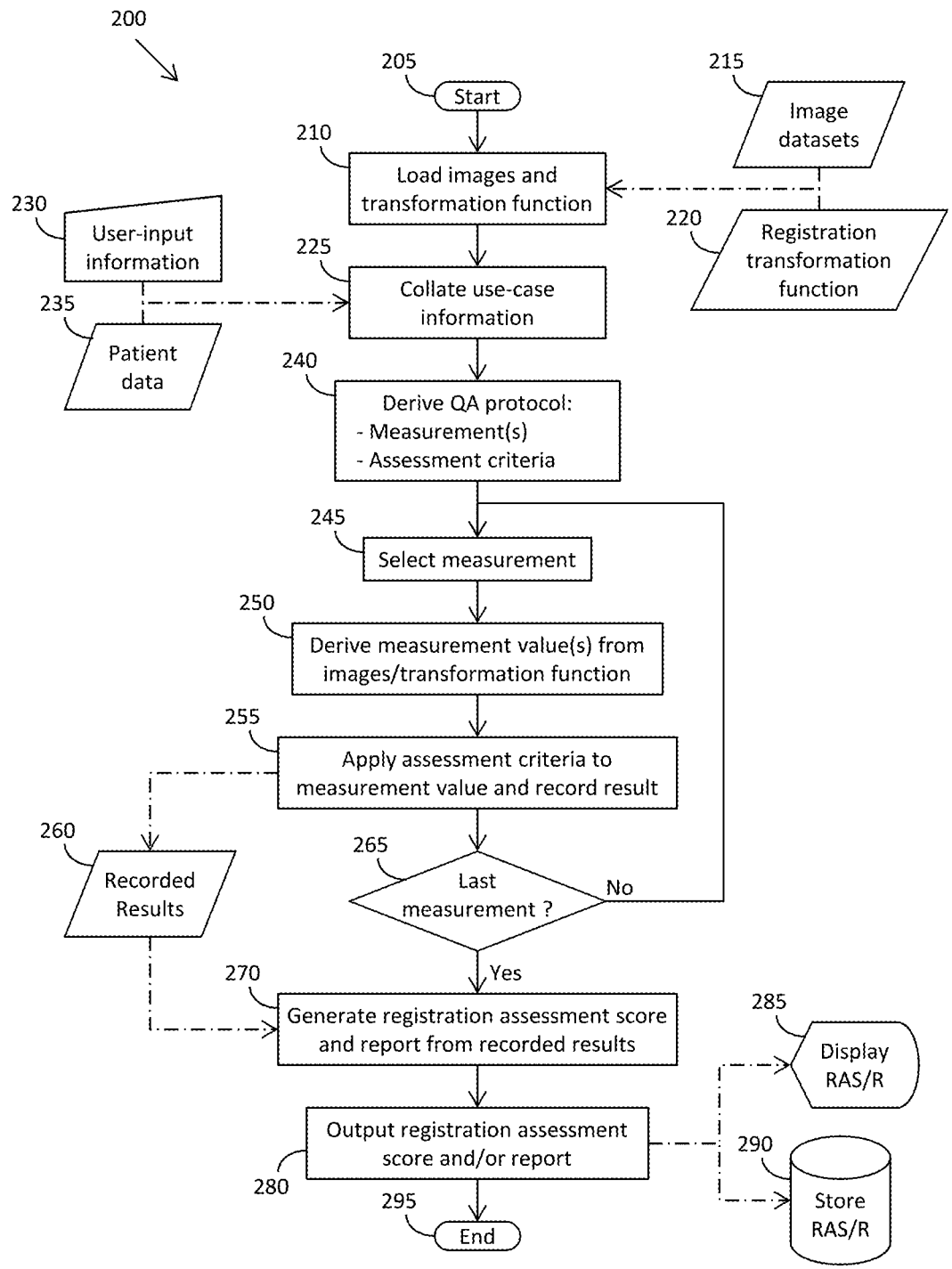
FIG. 2 illustrates a simplified flowchart of an example of a method of assessing image registration between a first medical image and a second medical image.

FIG. 2 illustrates a simplified flowchart 200 of an example of a method of assessing image registration between a first medical image (often referred to as the source or fixed image) and a second medical image (often referred to as the target or moving image) according to some examples of the present invention, and such as may be performed by the medical imaging system 100 of FIG. 1.

The method starts at 205 and moves on to 210 where the image datasets 215 for the medical images are loaded or otherwise obtained, along with registration data representing the registration from the source/fixed medical image to the target/moving medical image. In the illustrated example, the registration data is in the form of a transformation function 220. The image datasets 215 and registration data 220 may be loaded from local memory, for example from the memory element 125 in FIG. 1, or from external data storage such as the database 120 in FIG. 1. In some alternative examples, the registration data 220 may be obtained directly from execution of the registration algorithm by the same system performing the method of FIG. 2.

The image datasets 215 may have been acquired through any of a variety of modalities, such as CT (computed tomography), PET (positron emission tomography), SPECT (single photon emission computed tomography), MRI (magnetic resonance imaging), ultrasound, radiography, portal images from linear accelerators, etc., and may comprise 2D (planar) and/or 3D (volumetric) image datasets.

The transformation function comprises parameters for the transformation model that was used in the particular registration algorithm responsible for the registration from the target/fixed medical image to the source/moving medical image. For example, in the case of a 3D rigid registration, there would be three translation parameters and three rotation parameters that would specify the transformation. In the case of a deformable registration algorithm, there are typically many more parameters; potentially a vector at each voxel of the 3D volume. In this case, by convention each vector specifies the shift that must be applied to that voxel in the source image to find the corresponding location in the target image.

Use-case information is collated, at 225. Such use-case information may comprise, for example, information relating to one or more of:
- the clinical task being performed,
- the clinical question of interest,
- the disease such as its location, extent and stage,
- the patient such as sex, age, prior treatment,
- one or more regions of interest,
- etc.

The use case information may be obtained in any suitable manner. For example, and as illustrated in FIG. 2, the use case information may include information input by the user (i.e. clinician) 230 and/or information obtained from patient records 235. Such patient records 235 may be loaded from local memory, for example from the memory element 125 in FIG. 1, or from one or more external data storage devices such as the database 120 in FIG. 1.

Having collated the use-case information, a quality assessment protocol is derived comprising a set of measurements and assessment criteria therefor that will be used to assess the quality/accuracy of the registration between the medical images.

A wide range of measurements may be used to assess the quality/accuracy of the registration between the medical images. A first category of measurement may include measurements that measure the biological plausibility of the deformation field. Examples of such biological plausibility measurements include:
(i) smoothness of the deformation field,
(ii) volume preservation,
(iii) local rigidity,
(iv) the determinant of the Jacobian (a matrix comprised of the partial derivatives of the deformation field with respect to its coordinates),
(v) the divergence of the deformation field (a measure of the rate of change of the deformation field),
(vi) the curl of the deformation field (a measure of the rotation of an area of the deformation field),
(vii) the harmonic energy of the deformation field (a measure of the variability of the deformation field defined as the sum of the squares of the elements of the Jacobian Matrix),
(viii) the strain of the deformation field (a measure of the local shearing induced by the deformation field and can be used to measure local rigidity), and
(ix) the shear angle of the deformation field.

Such measurements may be used to provide an indication of the plausibility of the deformation of the registration from the first image to the second image with respect to prior models of deformation.

A second category of measurements may include surrogate measures of anatomical matching accuracy. Examples of such measurements include:
(i) local intensity difference,
(ii) mutual information (a standard measure of statistical similarity between the images and datasets), and
(iii) cross-correlation (a measure of the similarity of the images and datasets).

We refer to these as surrogate measures of anatomical matching because they do not measure the error in known anatomical locations, but instead measure the similarity of the appearance of the matched images.

A third category of measurements may include numerical properties of the registration result itself. Such measures try to measure the numerical result itself rather than its anatomical correctness. For example, most registration algorithms are based on optimisation methods that do not guarantee converging on the global optimum (the best solution over all parameter values). Therefore, testing the stability of the solution can help assess the validity of the result. Examples of such numerical properties include testing the stability and empirical invertibility of the result. Registration is typically an optimization algorithm, whereby the algorithm attempts to optimize particular characteristics over a (large) range of parameters. A stable result is one for which a small change in the parameters does not result in a large change in the characteristics to be optimised. Stability can be measured by perturbing the parameters of the deformation field and measuring the change in the characteristics to be optimised.

Invertibility can be measured either empirically by testing which points can be inverted using a standard inversion algorithm or analytically using the determinant of the Jacobian. The Jacobian is a standard measure of vector fields and here it may be used to measure properties of the deformation field. The Jacobian is a matrix comprised of the partial derivatives of the deformation field with respect to its coordinates. So, for a 3D deformation field it will measure the amount of change in the deformation field as a function of x, y, z. It characterizes the vector field. If the value is non-zero then it is invertible which means that the user can expect consistent behaviour when transforming a point, A1, from the source image to a point, B1, in the target image, and vice versa from B1 to A1. If it is invertible then A1 should map to B1 and B1 should map back to A1 when using the inverse transform. The determinant of the Jacobian can also measure whether the deformation is creating a volume expanding or contracting effect locally. This means that different aspects of the deformation field can be measured and constraints applied on them.

The quality assessment protocol derived at 240 may comprise a set of measurements containing one or more measurements, and in particular containing a plurality of measurements for assessing the quality/accuracy of the registration performed between the two medical images.

The biomechanical properties of each type of tissue in the human body are different and can be used to assess the validity of registration results. For example, bones can be expected to move rigidly in an articulated fashion, but not to change in volume. Similarly, soft tissue should not compress or expand in volume, whilst areas filled with air, such as the lungs, can change in volume. Thus, different measures can be used for different regions of the body and/or tissue type to assess the validity of registration results. Accordingly, in some examples, some measurements may be associated with a particular tissue type or types, whilst other measurements may be associated with all types, such as measurements of numerical invertibility.

Figure 3:
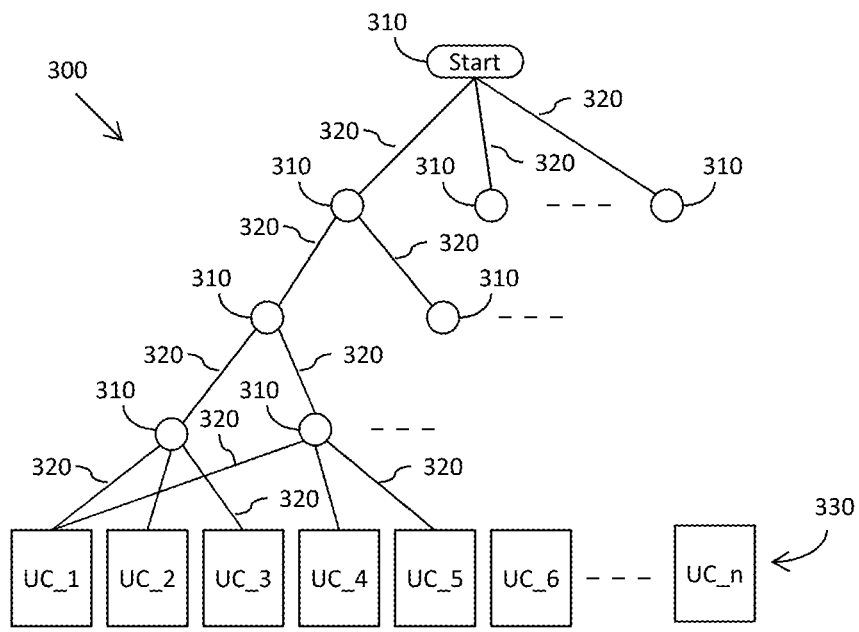
FIG. 3 illustrates an example of a tree structure for deriving quality assessment protocols.

The quality assessment protocol may be derived by selecting a predefined quality assessment protocol from a plurality of predefined quality assessment protocols. For example, each of the predefined quality assessment protocols may comprise a particular set of measurements relevant to one or more predefined use-case scenario(s) associated therewith. The predefined use-case scenario that most closely matches the collated use-case information may be identified, and the quality assessment protocol with which the identified use-case scenario is associated may then be extracted from, say, local memory such as the memory element 125 in FIG. 1, or from external data storage such as the database 120 in FIG. 1. For example, and as illustrated in FIG. 3, the collated use-case information may be used to descend through a tree structure 300, whereby at each node 310 the collated use-case information is used to select a branch 320 to follow down to the next node 310 until a leaf node 330 representing a predefined use-case scenario is reached. The quality assessment protocol with which the predefined use-case scenario of the arrived at leaf node 330 is associated may then be extracted.

Figure 4:
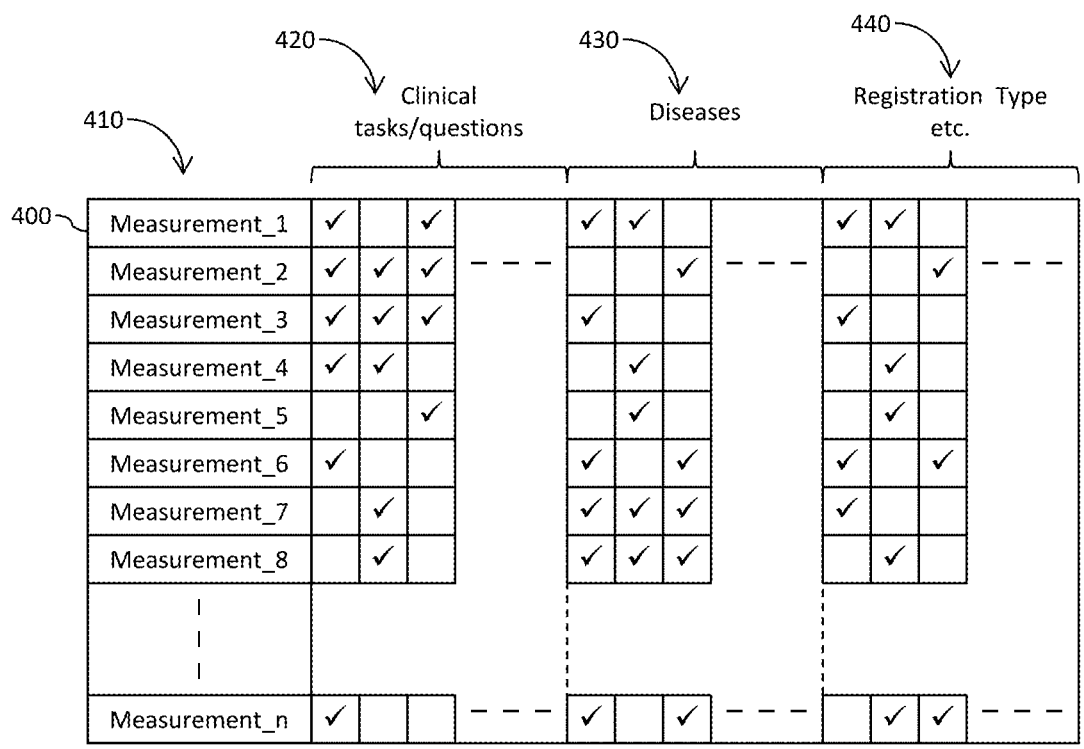
FIG. 4 illustrates an example of a quality assessment protocol generation table deriving quality assessment protocols.

Alternatively, the quality assessment protocol may be specifically generated based on the current use-case information, for example by selecting a set of measurements predefined as being relevant to use-case parameters within the collated use-case information. For example, and as illustrated in FIG. 4, one or more quality assessment protocol generation table(s) 400 may be pre-configured with potential measurements 410. The quality assessment protocol generation table(s) 400 may further be pre-configured to identify particular use-case parameters to which individual measurements are relevant. For example, and as illustrated in FIG. 4, the quality assessment protocol generation table(s) 400 may include (in the illustrated example) columns representing particular clinical tasks and/or questions 420, diseases 430, registration types (e.g. rigid, affine, deformable) 440, etc. For each measurement 410, the quality assessment protocol generation table(s) 400 may be configured to indicate whether the respective measurement is relevant to each of the use-case parameters. A quality assessment protocol may thus be generated by comparing the current use-case information to the quality assessment protocol generation table(s) 400, and a set of measurements for the quality assessment protocol comprising those measurements 410 indicated as being relevant to at least one use-case parameter, or at least one from each use-case parameter category, within the current use-case.

Assessment criteria for each measurement of the quality assessment protocol must also be derived. Such assessment criteria are used to assess the measurements to produce an indication of the accuracy of the registration. In its simplest form, such assessment criteria could be a simple threshold or range of values used to define a criterion for a particular measurement. More sophisticated methods may use prior probability distributions for the measurements and utilize statistical tests to assess each measurement under a certain confidence interval. In some examples, the assessment criteria may be derived based on use-case information such as, say, temporal spacing of the images, patient details, disease information, modality and image acquisition information, etc. Accordingly, it is contemplated that the assessment criteria for individual measurements may be derived based on one of more of:
- a predefined fixed threshold value;
- a predefined fixed range;
- a threshold value derived from the collated use-case information;
- a threshold range derived from the collated use-case information;
- probability distributions derived from prior statistical tests;
- etc.

One example of a particular use-case scenario is a PET/CT guided target delineation in the head and neck of a patient. In external beam radiation therapy, the aim is to deliver the prescribed radiation dose to the target region, i.e. a tumour, whilst minimising the dose to surrounding regions, the organs-at-risk. As part of the therapy planning process, it is necessary to delineate both the target region and the organs-at-risk on a scan of the patient, known as the planning volume. This scan is typically a CT image and is acquired whilst the patient is positioned in the same way as they would be on the day of treatment. For Head and Neck cancer, this might typically involve the use of a thermoplastic mask moulded over the patients head and fastened to the flat treatment table. This is done in order to minimise motion during treatment and to ensure that the patient is positioned consistently throughout the weeks of therapy.

The use of PET/CT has been shown to improve the accuracy and consistency of target delineation in radiation therapy planning. While many sites do not have access to a dedicated PET/CT for therapy planning, a PET/CT is often performed as part of the diagnostic process (a few weeks before treatment planning), though this is typically not performed whilst the patient is setup in treatment position. In addition, the patient couch used for diagnostic scans is curved (for comfort) whereas the couch used for treatment is flat, all of which has the consequence that there can be a significant misalignment between the diagnostic PET/CT and planning CT. Therefore it is desirable to perform a deformable registration between the two sets of scans to bring the PET/CT into alignment with the planning CT. Typically, this is performed by aligning the CT of the PET/CT with the planning CT and using the same deformation field to align the PET of the PET/CT; the assumption is that the PET and CT of the PET/CT are acquired without any patient motion (usually a reasonable assumption).

Since the PET/CT and planning CT are typically acquired within a few weeks of each other, one can assume that the anatomy in the head and neck region has not changed significantly. In fact if it has, this would be a reason not to use the PET/CT.

The appropriate quality assessment protocol for this situation could be as follows:

TABLE 1

| Property to be measured | Measurement | Criteria |
| --- | --- | --- |
| Volume is preserved in soft tissue including fat | Determinant of the Jacobian within −150 HU and 160 HU | Between 0.9 and 1.1 over the whole scan |
| Bones are moved rigidly | Divergence of the Deformation Field within 160 HU and 3000 HU | Between −0.01 and 0.01 over the whole scan |
| Appearance is well matched | Local Cross-correlation | >0.8 over the whole scan |
| Deformation Field is invertible | Empirical Invertibility—Fraction of points that have a residual error < 1 mm | >0.9 over the whole scan |

The system may select, or otherwise derive this set of measurements and criteria therefor based on use-case information such as the dates of the PET/CT and the Planning CT along with some application context such as entering an Image Guided Contouring mode. Most treatment planning and contouring systems require that the user initiates such a mode in order to perform this task. The anatomical location of the disease can be obtained from the Oncology Information System which records such patient information.

A further example of a particular use-case scenario is MRI guided target definition in prostate. This is a similar clinical use-case to the first. However, we are focussing within the pelvic region and the PET/CT is substituted with an MRI. As with the previous example, we can assume that the MRI and planning CT are acquired within a few weeks of each other. However the contents of bladder and colo-rectum can cause large differences between the anatomy in the two scans. The effect of differences in bladder filling is to move nearby organs causing local deformations. Since the colo-rectum can be empty, filled with air pockets or stools, the anatomy here is unlikely to match between the MRI and planning CT. Therefore one should not use volume preservation within these two regions to assess the registration quality. Since the bladder and colo-rectum are delineated as part of treatment planning, we can expect to use those regions as part of the quality assessment protocol derivation.

Since the registration is multi-modality it would be appropriate to use Mutual Information as a measure of the appearance match instead of cross-correlation. The appropriate quality assessment protocol for this situation could be as follows:

TABLE 2

| Property to be measured | Measurement | Criteria |
|---|---|---|
| Volume is preserved in soft tissue including fat excluding Bladder and Colo-rectum | Determinant of the Jacobian within −150 HU and 160 HU | Between 0.9 and 1.1 outside the Bladder and Colo-Rectum regions |
| Bones are moved rigidly | Divergence of the Deformation Field within 160 HU and 3000 HU | Between −0.01 and 0.01 over the whole scan |
| Appearance is well matched | Normalised Pointwise Mutual Information—Fraction of points that > 0.95 | >0.9 over the whole scan |
| Deformation Field is invertible | Empirical Invertibility—Fraction of points that have a residual error < 1 mm | >0.9 over the whole scan |

The system may select, or otherwise derive this set of measurements and criteria therefor based on use-case information such as the dates of the MRI and the Planning CT along with some application context such as entering an Image Guided Contouring mode. The anatomical location of the disease can be obtained from the Oncology Information System which records such patient information.

A still further example of a particular use-case scenario is longitudinal analysis of response to therapy in Lung cancer. In this use-case the task is to assess changes to the patient's anatomy as a result of cancer therapy. Such therapy might be radiation based or chemotherapy or combination of both. In the case of the former the purpose might be to monitor the patient during the course of therapy in order to ensure the continued validity of the treatment plan despite tumour shrinkage and possible weight loss. Since radiation therapy is often administered over 6 weeks, such changes might render the original plan sub-optimal or even dangerous.

In this situation, one would expect, and indeed hope for, changes in tumour volume. In addition, cancer patients tend to lose weight during therapy and therefore this should also be accounted for. However, one would expect most of this loss to be in the fatty tissue rather than non-fatty tissue. Bones should move rigidly and the appearance should be well matched. One would also expect that the volume of the lungs changes.

A suitable quality assessment protocol for this use-case might be:

TABLE 3

| Property to be measured | Measurement | Criteria |
|---|---|---|
| Volume is preserved in non-fatty tissue except within the lungs and tumour region (Planning Target Region—PTV) | Determinant of the Jacobian within 10 HU and 160 HU | Between 0.9 and 1.1 outside the lungs and outside the tumor target area (Planning Target Volume—PTV) |
| Bones are moved rigidly | Divergence of the Deformation Field within 160 HU and 3000 HU | Between −0.01 and 0.01 over the whole scan |
| Appearance is well matched | Normalised Sum-squared difference between the images | <0.1 |
| Deformation Field is invertible | Empirical Invertibility—Fraction of points that have a residual error < 1 mm | >0.9 over the whole scan |

The system may select, or otherwise derive this set of measurements and criteria therefor based on use-case information such as the dates of the Planning CT and those of the follow-up images along with some application context such as entering a Treatment Monitoring mode. The anatomical location of the disease can be obtained from the Oncology Information System which records such patient information, or inferred from the existing treatment plan.

A still further example of a particular use-case scenario is multiple treatment dose summation for re-treatment decision support in Lung cancer. In this example, the task is to support the user in making a re-treatment decision. The patient would have been treated previously by one or more courses of radiation therapy and due to recurring disease the task is now to assess whether it is possible to treat them further. Such decisions require an estimate of the total dose delivered, including all previous and any proposed treatments, and often hinge on the dose to particular organs-at-risk. For example, in Lung cancer this might be the dose to the heart or to the spinal cord (or both), whereas in Head and Neck cancer it might be the dose to the parotids.

The user would first register the previous planning volumes to the latest planning volume, then, after registration quality assessment using the invention, proceed to sum up the corresponding dose volumes to produce a total dose.

A suitable quality assessment protocol could be similar to the treatment monitoring case except that one would focus mostly on the dose limiting structures, i.e. those structures that are close to reaching their limit:

The system may select, or otherwise derive this set of measurements and criteria therefor based on use-case information such as the dates of the Planning CTs along with some application context such as entering a Dose Summation mode. The anatomical location of the disease can be obtained from the Oncology Information System which records such patient information, or inferred from the existing treatment plans.

Referring back to FIG. 2, having derived the quality assessment protocol to be used, comprising a set of measurements and assessment criteria therefor, the method moves on to 245 where a first measurement from the quality assessment protocol is selected. One or more measurement value(s) for the selected measurement are then calculated or otherwise derived from the medical images and/or registration information, at 250. The assessment criteria for the selected measurement is/are then applied to the derived measurement value(s), at 255, and the result(s) of applying the assessment criteria to the derived measurement value(s) is/are recorded, at 260. The recorded results may comprise simple pass/fail indications, or accuracy ratings such as percentage pass/fail values. In the illustrated example, if further measurements are required to be derived and assessed at 265, the method loops back to 245 where a next measurement is selected. However, once an assessment result for the last measurement has been recorded, the method moves on to 270 where, in the illustrated example, a registration assessment score is generated from the recorded results 260.

TABLE 4

| Property to be measured | Measurement | Criteria |
|---|---|---|
| Volume is preserved in non-fatty tissue except within the lungs and tumour region (Planning Target Region—PTV) | Determinant of the Jacobian within 10 HU and 160 HU | Between 0.9 and 1.1 outside the lungs and outside the tumor target area (Planning Target Volume—PTV) |
| Bones are moved rigidly | Divergence of the Deformation Field within 160 HU and 3000 HU | Between −0.01 and 0.01 over the whole scan |
| Appearance is well matched | Normalised Pointwise Mutual Information—Fraction of points that > 0.95 | >0.9 over the whole scan |
| Deformation Field is invertible | Empirical Invertibility—Fraction of points that have a residual error < 1 mm | >0.9 over the whole scan |
| Dose limiting structure is locally rigid | Divergence of the Deformation Field over all HU | Between −0.01 and 0.01 for the dose limiting structure |

In its simplest form, the registration assessment score may comprise the fraction of the measurements that were within specified tolerances. However, it is contemplated that the registration assessment score may be collated in a variety of other ways to produce a single score. Such methods may include, but are not limited to:
 summation,
 averaging,
 weighted averaging, and
 using machine learning approaches to evolve a model of the importance of each to the overall score.

The method of collation may be use-case dependent, and thus may be performed or configured differently depending on parameters within the collated use-case information. Such configuration may include varying the weighting between the measurements relative importance, thereby placing more importance on some measurements than others.

In the illustrated example, the recorded results are further used to generate a registration assessment report. For example, such a report might be in the form of a report specifying individual tests (measurement, tissue type and region), the criterion and whether they passed or failed. To aid interpretation, the results 260 should be described in a clinically relevant manner. Accordingly, the report may translate measurements to clinically relevant details such as, say, representing the determinant of the Jacobian between 300-800 HU as "volume change in bone". Since each quality assessment protocol may typically be relevant to particular use-case scenarios, a report for a particular protocol can be designed to provide additional contextual information to the user. For example, the report may be generated to explain why a certain measurement is important in the specific use-case or provide caveats for the information. In this manner, when a less than optimal registration assessment score is reported, the report can also provide an indication of the reason. For example, if the divergence of the deformation field is above a pre-configured threshold, and thus its contribution to the final score is to reduce the final score, the report may include an entry of, say, "Registration quality is low due to a large change of volume". The report may also identify the measurement causing the largest reduction in the quality score, or against all measurements reducing the score, or for measurements whose score reduction is considered a "significant" reduction for the current use-case defined through configuration or other setup. The importance of individual measurements vary with use-case as the importance of the physical meaning is more or less appropriate, thus the reasoning presented associated with each feature may be adapted according to the current use-case.

Having generated the registration assessment score and report, the method moves on to 280 where the generated registration assessment score and report are output, for example by being stored within a data storage device such as within local memory, for example within the memory element 125 in FIG. 1, or with external data storage such as the database 120 in FIG. 1. Additionally/alternatively the registration assessment score and report may be output by being displayed 285 to a user on a display screen, such as on a screen of the display 160 in FIG. 1. For example, the registration assessment score and/or report may be displayed graphically to the user in the form of a colour coding overlaid over one or more of the medical images, or with quantitative information highlighted. Areas of concern that don't pass the criteria may also be highlight to the user.

The method of the illustrated example then ends, at 295.

Advantageously, the method illustrated in FIG. 2 and described above utilises a use-case relevant quality assessment protocol (i.e. a set of tests and assessment criteria therefor relevant to the particular use-case) to assess the accuracy of the registration between two medical images. This enables image registration accuracy to be assessed in a quantitative manner across a range of clinical applications in a focussed and disease specific manner.

Figure 5:
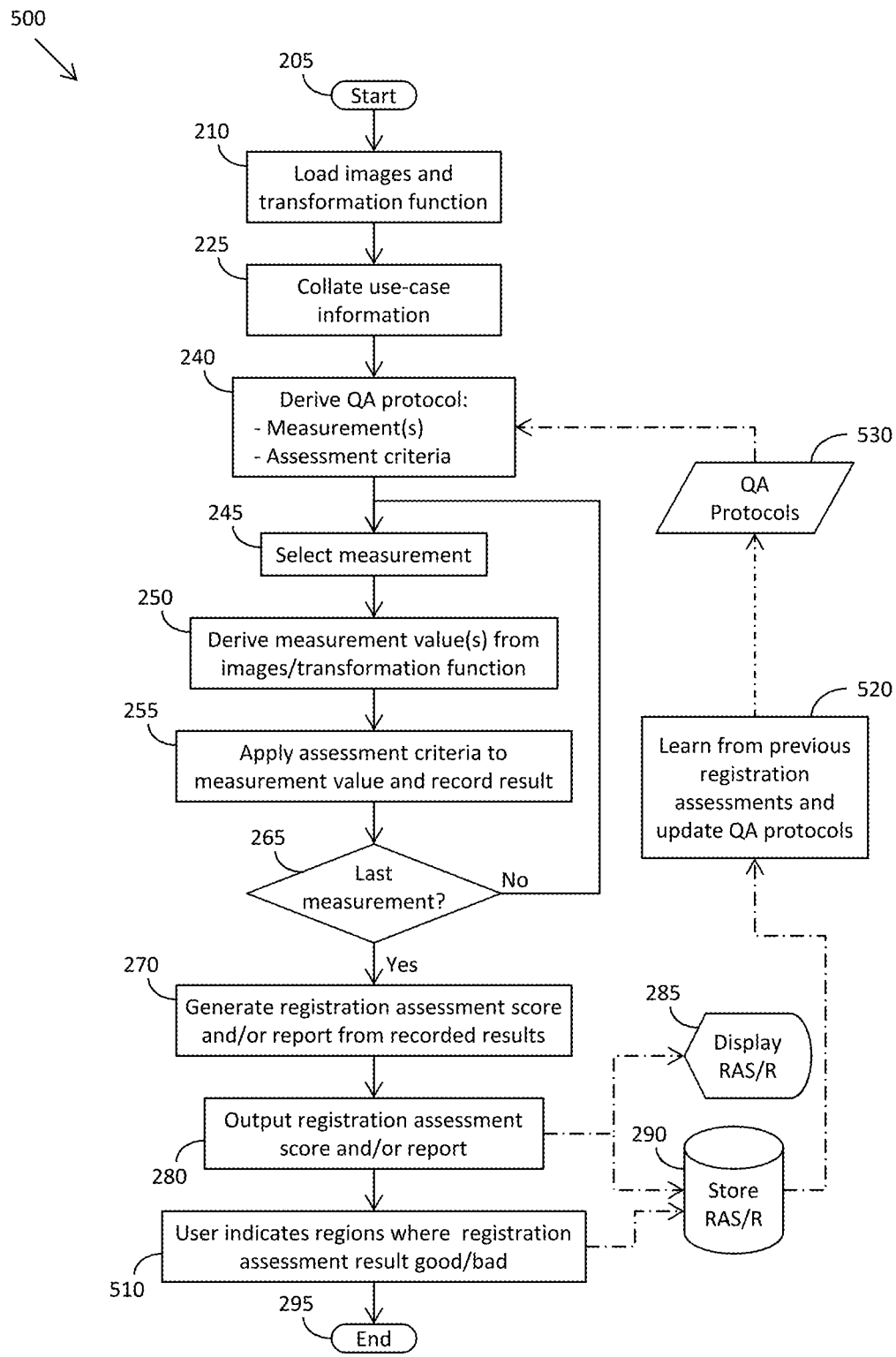
FIG. 5 illustrates a simplified flowchart of an alternative example of a method of assessing image registration between a first medical image and a second medical image.

FIG. 5 illustrates a simplified flowchart 500 of an alternative example of a method of assessing image registration between a first medical image and a second medical image. In FIG. 5, analogous steps to those of the method of FIG. 2 have retained the same numbering as in FIG. 2. Where the alternative example method illustrated in FIG. 5 differs from the method of FIG. 2 is by virtue of user feedback being used to enable the quality assessment protocols used in the future to be improved.

For example, it may be preferable in some situations to provide means for the user to identify which results were good and which were bad, and to enable the system to automatically learn which tests and what criteria are most relevant for particular use-case scenarios. This may be achieved by utilizing standard machine learning methods to perform "feature selection"; that is selecting only those tests that separate the good results from the bad ones. Examples of such machine learning methods include Feature Selection techniques. Feature Selection techniques operate by evaluating the predictive power of the system over different sub-sets of features and selecting those that have the best performance. A simple approach might be to use Brute-force search where all possible combinations are evaluated. Another, more efficient, approach might be to use a Greedy Algorithm which first selects the best single feature and then adds the best second feature and so on. Alternatively, the system could learn only the criteria for a specified set of tests. This could be done by building distributions of the measurement values during a training phase (or even during its regular use) and testing any new cases against those distributions.

Accordingly, in the example method illustrated in FIG. 5, the method comprises a user indicating regions where the registration assessment result is good and/or bad, at 510. The user provided indications of good/bad regions may then be stored along with the registration assessment result. Subsequently, a learning algorithm may be implemented, at 520, which uses the user provided indications of good/bad registration assessment to update quality assessment data 530 subsequently used to derive quality assessment protocols used in future registration assessments.

In some alternative examples, it is contemplated that the user may be allowed to review and override particular results. For example, if the system highlights that a particular test failed, the user could indicate to the system to disregard the result and to record a reason for this. In this manner, any subsequent reviewer or user of the registration result can be informed of this decision and its justification. For example, a user might override a particular failed region because it is irrelevant to this particular patient's situation.

Although the present invention does not require a user to provide ground-truth annotations of corresponding locations, if such measurement were provided then the system could also test these and provide a summary in the report.

Such ground-truth annotations may be provided as part of the loaded image datasets, or provided by the user at run-time.

Referring now to FIGS. 6 to 10, there is illustrated a more detailed example of a practical implementation of the present invention. The use-case for the example illustrated in FIGS. 6 to 10 relates to the registration of two CT images for the purpose summation of dose for two lung treatments. The clinical task to be performed is to assess the total dose that would be delivered to the spinal cord, an organ at risk, when planning a new radiotherapy treatment, taking into account the dose delivered in the previous treatment.

Figure 6:
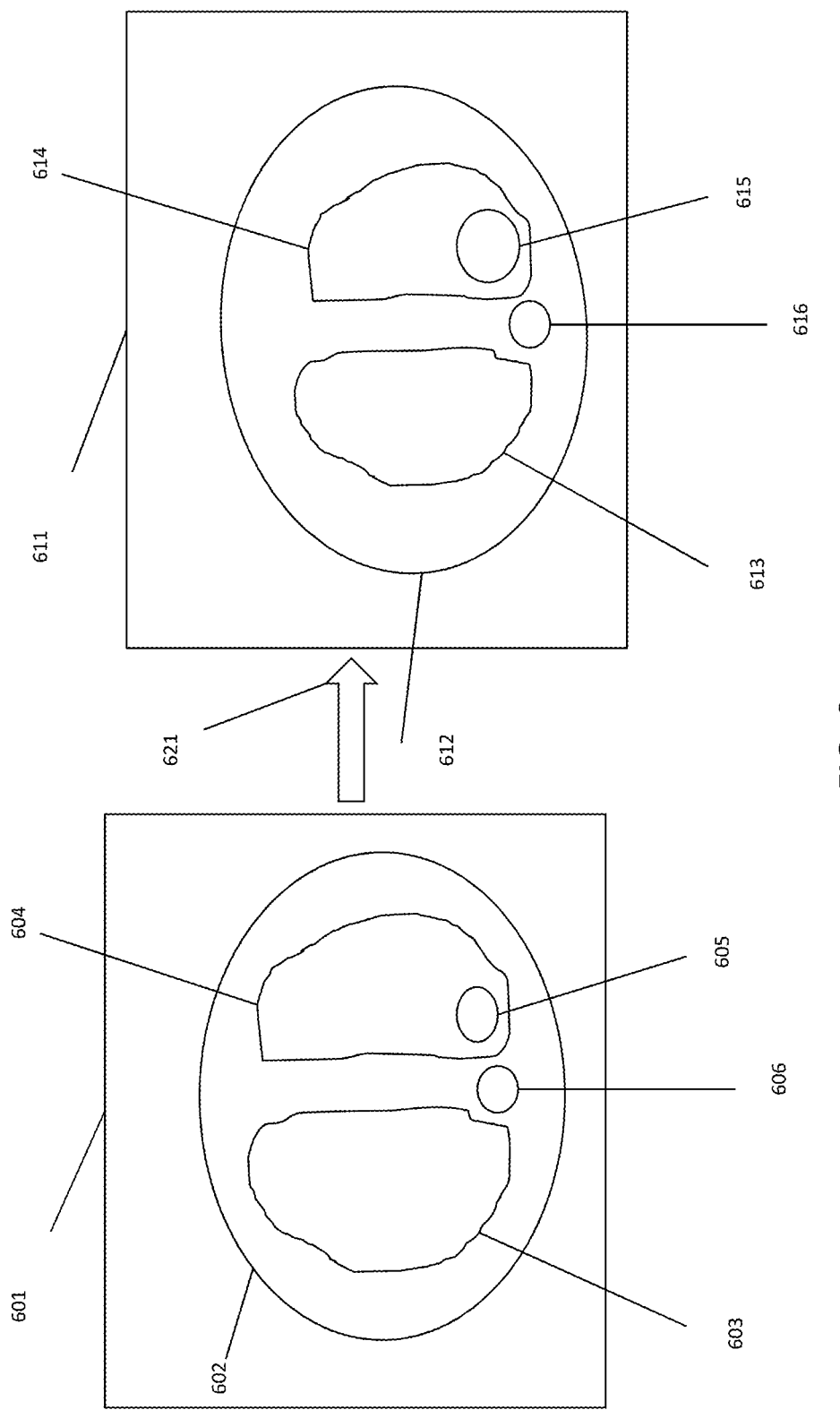
FIG. 6 to FIG. 10 illustrate a detailed example of a practical implementation of the present invention.
Figure 7:
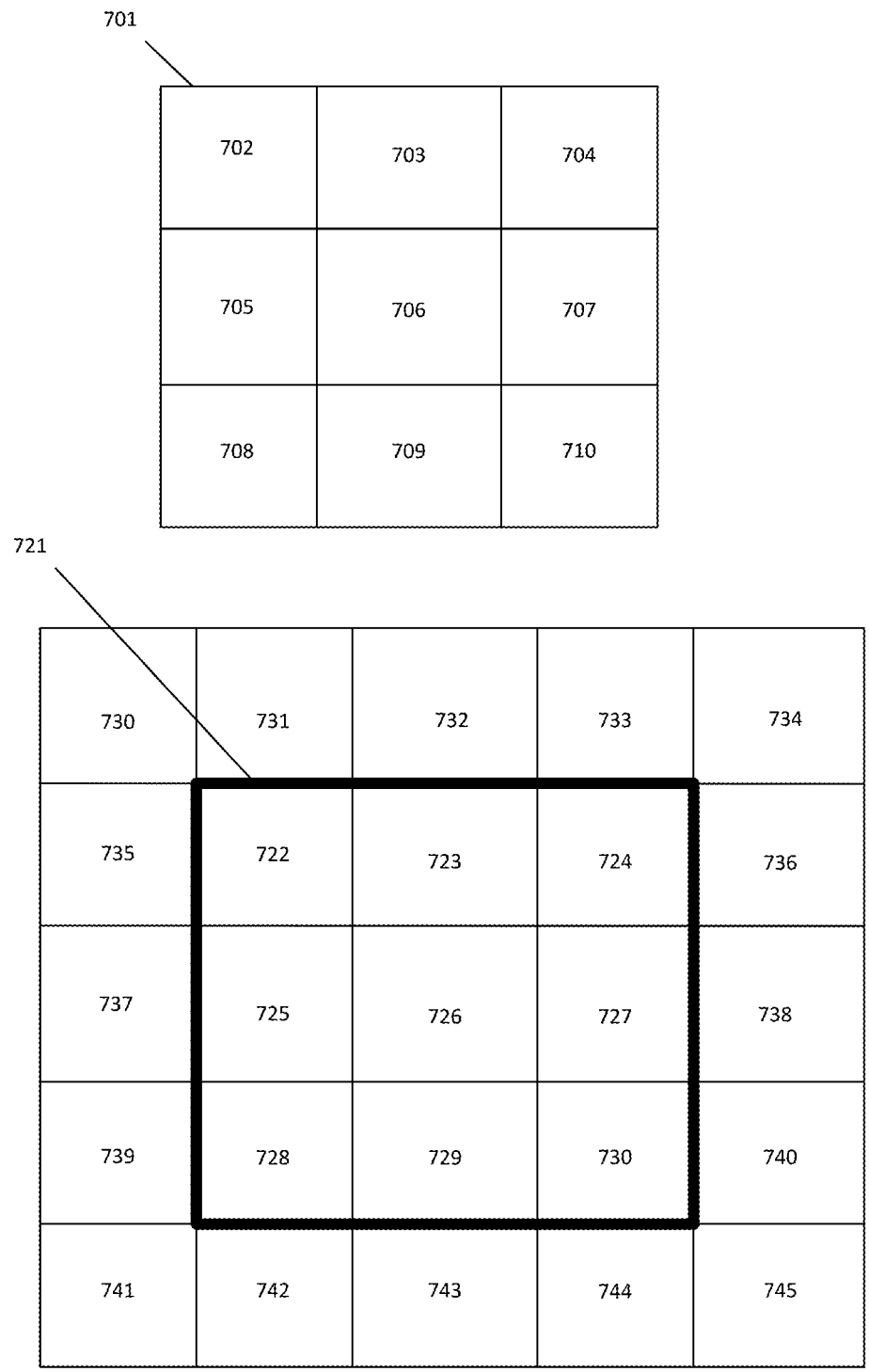
Figure 8:
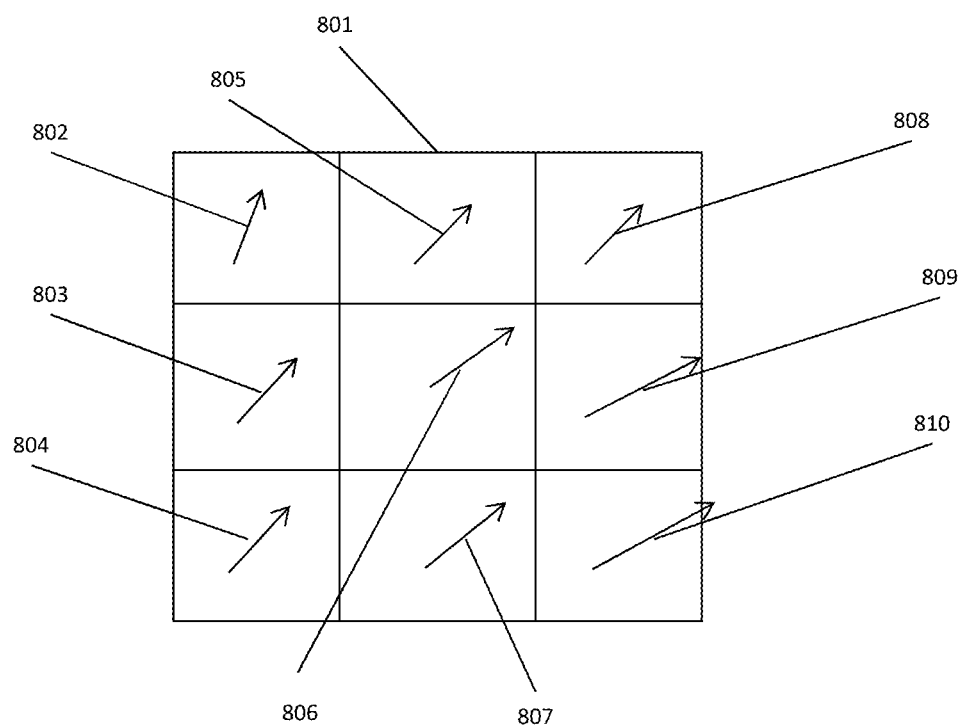

FIG. 6 illustrates the registration performed. A volumetric CT image 601, on which the original radiotherapy treatment was planned is deformably registered (indicated by arrow 621) to another CT image 611 on which the new radiotherapy treatment will be planned.

Each image 601, 611 shows corresponding anatomy: the patient body 602 & 612), two lungs 603, 604 & 613, 614), the spine 606 & 616) and the tumor being treated 605 & 615). However, the position, size and shape in each image vary as a result of patient motion, tumor growth/shrinking, breathing position etc.

Once the registration is performed, the clinician may need to assess if they can trust the registration between the images to assist in summing the planned dose for the two plans correctly for the spinal cord.

The system loads the images 601, 611 and the registration information 621. Additionally a region 606 corresponding to the spinal cord is indicated on image 601 and is sent to the system.

The system calculates the measurements for the images and the registrations for each voxel of image 601 as follows.

Figure 9:
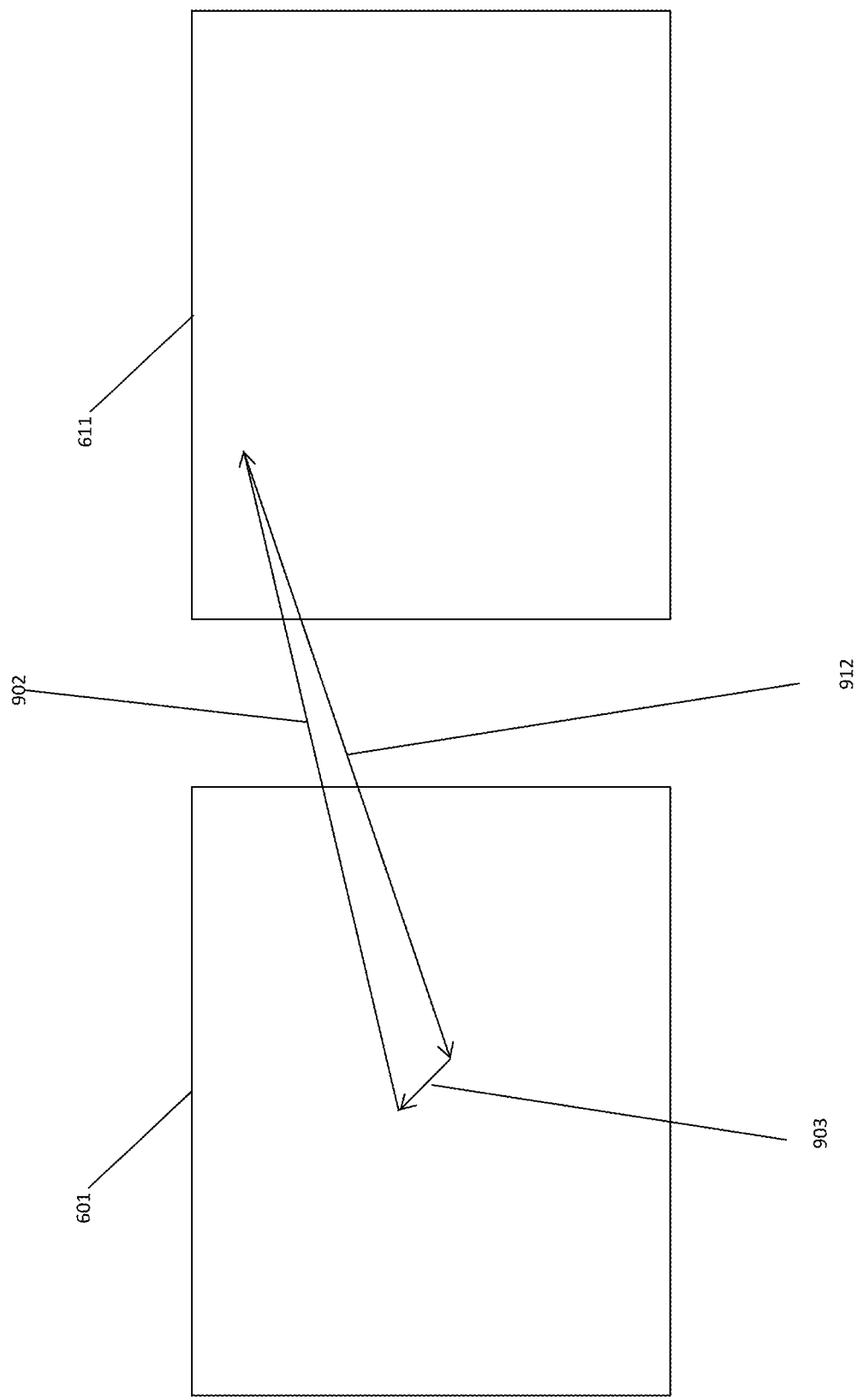

Image 601 is deformed and resampled using the registration onto Image 611. For each voxel in image 601, a patch 701 (FIG. 7) around the voxel is compared to the corresponding patch 721 in Image 611. The sum-squared-difference (SSD) of intensity values is calculated. The patch is perturbed such that the centre voxel 706 now matches each of the nearby voxels (e.g. 722-725 & 727-745) in turn and the SSD for the patch is computed again. This is performed up to a distance of, say, 10 mm away from the original voxel 726. The minimum SSD is found, and the distance of the centre of the patch where the minimum SSD is found from the original voxel 726 is measured. The difference in value of the SSD and it local minimum value is calculated. For each voxel in image 601 the deformation vector field 802-810 (FIG. 8) is assessed in a patch 801. The divergence and curl are calculated. As illustrated in FIG. 9, at each voxel the forward deformation 902 maps from image 601 to image 611. For each voxel in image 601 an empirical estimate of the inverse deformation 912 which should map from image 611 back to image 601 is made using a simple scheme. A measure of the invertability is calculated as the distance error in inversion 903.

Thus the system has calculated six measures on a voxel wise basis:
  (i) SSD
  (ii) Difference of SSD to minimum local SSD
  (iii) Distance to local minimum SSD
  (iv) Divergence of deformation field
  (v) Curl of deformation field
  (vi) Inversion error The average and maximum value of each measurement is computed within the region of interest, leading to twelve regional measurements.

The system may then normalise and collate these twelve feature scores using, say, simple sigmoid functions configured previously by the user for this application and organ. Each of the twelve feature scores is mapped to the range 0-1, where 1 represents an acceptable feature score, and 0 represents an unacceptable feature score. The function is continuous allowing for marginal feature scores. The twelve scores are summed and then rescaled to be a percentage value.

Example scores for the twelve measurements are:

TABLE 5

| Feature | Average | Max |
| --- | --- | --- |
| SSD | .95 | .9 |
| Difference of SSD to minimum local SSD | .99 | .95 |
| Distance to local minimum SSD | .99 | .97 |
| Divergence of deformation field | .87 | .75 |
| Curl of deformation field | .86 | .6 |
| Inversion error | .92 | .91 |

Figure 10:
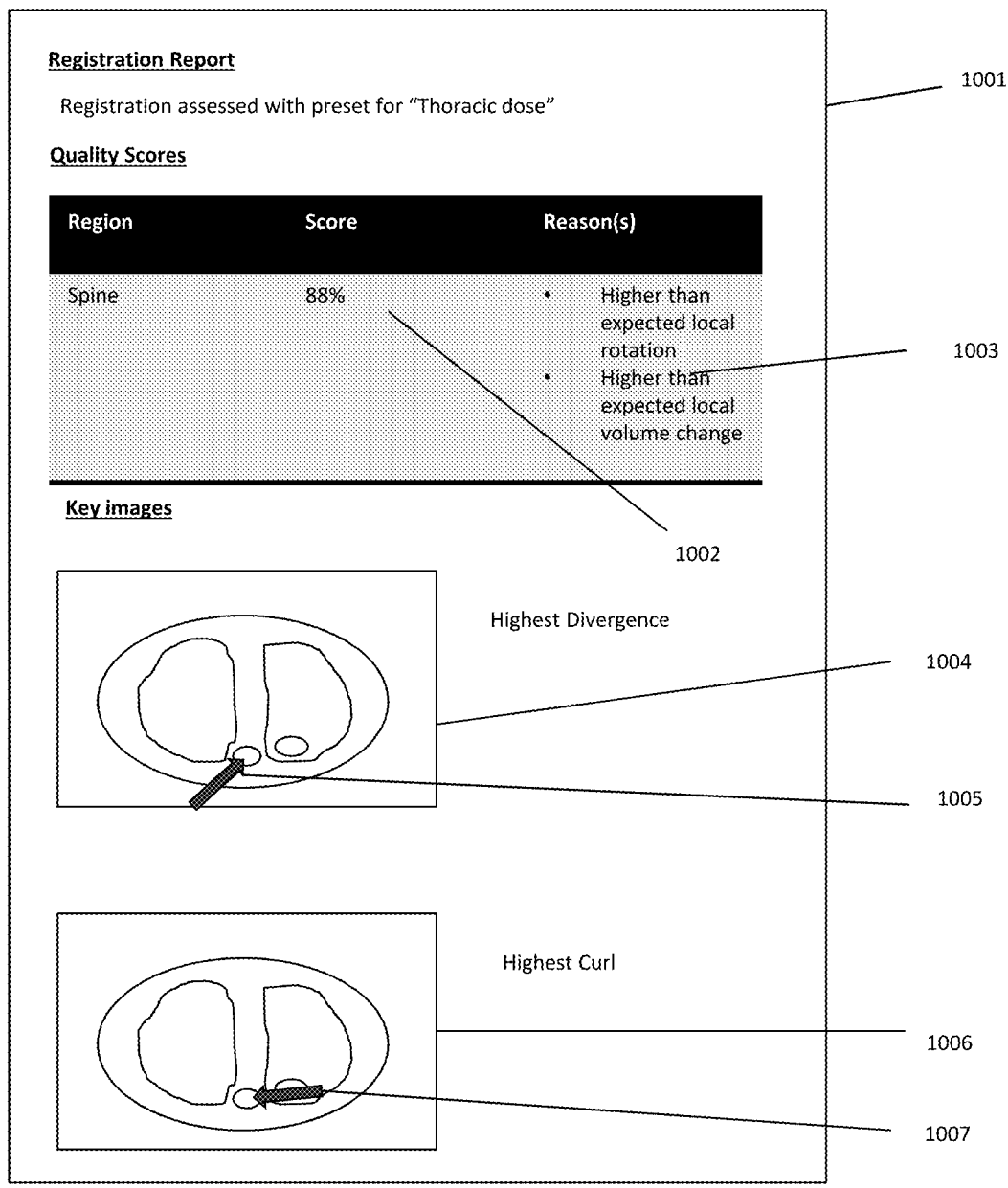

This leads to a registration quality score of 88%. The system reports that for the region of interest the registration quality score is 88%. FIG. 10 illustrates such a report 1001, showing the quality score 1002

The system reports that there is higher than expected local rotation as the maximum curl is the worst feature. The system also reports that there is "higher than expected local volume change" as the maximum divergence is beyond a user configured threshold. In FIG. 10 the reasoning is presented at 1003.

The system indicates to the user the locations with the maximum divergence and maximum curl within the region of interest, such that the user can inspect the deformation field within an interactive system. In this example such indication is given on screenshots 1004 and 1006 with arrows 1005 and 1007.

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media (e.g., CD-ROM, CD-R, etc.) and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

We claim:

1. A method of assessing an image registration result between a first medical image of a patient and a second medical image of the patient; the method comprising:
   obtaining image datasets for the first and second medical images of the patient;
   obtaining registration data representing the registration from the first medical image to the second medical image of the patient;
   collating clinical use-case information for which the image registration result is required;
   deriving a set of at least one measurement and assessment criteria therefor based at least partly on the collated use-case information;
   performing the at least one measurement on at least one of the obtained image datasets and the obtained registration data to derive at least one measurement value, wherein the at least one measurement value does not rely on the presence of ground-truth correspondences;
   applying the assessment criteria for the at least one measurement to the at least one measurement value to derive at least one assessment result; and
   outputting an indication of a clinical relevance of the registration between the first and second images of the patient to the clinical use-case based on the at least one assessment result, wherein the indication of the at least one assessment result comprises a registration assessment score generated from the at least one assessment result.

2. The method of claim 1, wherein the registration data comprises parameters for a transformation model of a registration algorithm used to perform the registration from the first medical image to the second medical image.

3. The method of claim 1, wherein the clinical use-case information comprises at least one of:
   information input by a user;
   information loaded from local memory; and
   information loaded from at least one external data storage device.

4. The method of claim 1, wherein the clinical use-case information comprises at least one of:
 information relating to a clinical task being performed;
 a clinical question being asked;
 information relating to a disease;
 information relating to a patient; and
 information relating to at least one region of interest.

5. The method of claim 1, wherein the set of at least one measurement and assessment criteria comprises at least one of:
 at least one measure of biological plausibility of a deformation field of the registration from the first medical image to the second medical image;
 wherein the at least one measure of biological plausibility is one or more of:
 (i) smoothness of the deformation field,
 (ii) volume preservation,
 (iii) local rigidity,
 (iv) a determinant of the Jacobian of the deformation field,
 (v) a divergence of the deformation field,
 (vi) a curl of the deformation field,
 (vii) a harmonic energy of the deformation field,
 (viii) a strain of the deformation field, and
 (ix) a shear angle of the deformation field,
 at least one surrogate measure of anatomical matching accuracy; and
 at least one numerical property of the registration.

6. The method of claim 1, wherein the set of at least one measurement and assessment criteria is derived by selecting a predefined set of at least one measurement from a plurality of predefined sets of at least one measurement.

7. The method of claim 6, wherein the set of at least one measurement and assessment criteria is derived by identifying a predefined clinical use-case scenario that most closely matches the collated clinical use-case information, and selecting a set of at least one measurement with which the identified clinical use-case scenario is associated.

8. The method of claim 1, wherein the set of at least one measurement and assessment criteria is derived by selecting a set of measurements predefined as being relevant to clinical use-case parameters within the collated clinical use-case information.

9. The method of claim 1, wherein the indication of the at least one assessment result comprises a registration assessment record.

10. The method of claim 1, wherein the indication of the at least one assessment result is output by being displayed on a screen to a user.

11. The method of claim 10, wherein the indication of the at least one assessment result comprises at least one of:
 displaying the at least one assessment result graphically to a user in the form of a colour coding overlaid over at least one of the medical images, and
 displaying the at least one assessment result graphically to a user with quantitative information highlighted over at least one of the medical images.

12. The method of claim 1, wherein the indication of the at least one assessment result is output by being stored within a data storage device.

13. The method of claim 1, wherein the method further comprises:
 receiving at least one indication from a user about the registration assessment result for at least one region; and
 updating quality assessment data used to derive quality assessment protocols based at least partly on the received at least one indication from a user about the registration assessment result for at least one region.

14. A medical imaging system comprising a user terminal including at least one image registration assessment component; the at least one image registration assessment component being arranged to:
 obtain image datasets for the first and second medical images of the same patient;
 obtain registration data representing the registration from the first medical image to the second medical image of the patient;
 collate clinical use-case information for the image registration;
 derive a set of at least one measurement and assessment criteria therefor based at least partly on the collated use-case information;
 perform the at least one measurement on at least one of the obtained image datasets and the obtained registration data to derive at least one measurement value, wherein the at least one measurement does not rely on a presence of ground-truth correspondences;
 apply the assessment criteria for the at least one measurement to the at least one measurement value to derive at least one assessment result; and
 output an indication of the clinical relevance of the registration between the first and second images of the patient to the clinical use-case based on the at least one assessment result, wherein the indication of the at least one assessment result comprises a registration assessment score generated from the at least one assessment result.

15. The medical imaging system of claim 14, wherein the registration data comprises parameters for a transformation model of a registration algorithm used to perform the registration from the first medical image to the second medical image.

16. A non-transitory computer program product having executable program code stored therein for assessing image registration, the program code operable for:
 obtaining image datasets for the first and second medical images of the same patient;
 obtaining registration data representing the registration from the first medical image to the second medical image of the patient;
 collating clinical use-case information for the image registration;
 deriving a set of at least one measurement and assessment criteria therefor based at least partly on the collated use-case information;
 performing the at least one measurement on at least one of the obtained image datasets and the obtained registration data to derive at least one measurement value, wherein the at least one measurement does not rely on a presence of ground truth correspondences
 applying the assessment criteria for the at least one measurement to the at least one measurement value to derive at least one assessment result; and
 outputting an indication of the clinical relevance of the registration between the first and second image of the patient to the clinical use-case based on the at least one assessment result wherein the indication of the at least one assessment result comprises a registration assessment score generated from the at least one assessment result.

17. The non-transitory computer program product of claim 16, wherein the non-transitory computer program product comprises at least one from a group including: a hard disk, a CD-ROM, an optical storage device, a magnetic storage device, a Read Only Memory (ROM), a Programmable Read Only Memory (PROM), an Erasable Programmable Read Only Memory (EPROM), an Electrically Erasable Programmable Read Only Memory (EEPROM), and a Flash memory.

* * * * *